United States Patent [19]
McNaughton

[11] Patent Number: 6,010,460
[45] Date of Patent: Jan. 4, 2000

[54] PEAK FLOW METERS

[75] Inventor: John Peter McNaughton, Harlow, United Kingdom

[73] Assignee: Clement Clark International, Ltd., Essex, United Kingdom

[21] Appl. No.: 09/017,286

[22] Filed: Feb. 2, 1998

[30]     Foreign Application Priority Data

Feb. 6, 1997 [GB] United Kingdom .................. 9702400

[51] Int. Cl.⁷ .................................................... A61N 5/00
[52] U.S. Cl. ............................. 600/538; 600/528; 482/13
[58] Field of Search ........................... 600/538, 529–534, 600/300; 482/13

[56]     References Cited

U.S. PATENT DOCUMENTS

| | | |
|---|---|---|
| 3,958,565 | 5/1976 | Wright . |
| 4,499,905 | 2/1985 | Greenberg et al. . |
| 5,224,487 | 7/1993 | Bellofatto et al. ...................... 600/538 |
| 5,246,010 | 9/1993 | Gazzara et al. . |
| 5,253,651 | 10/1993 | Stockwell et al. ...................... 600/538 |
| 5,540,234 | 7/1996 | Lalui . |
| 5,565,630 | 10/1996 | Shene . |

FOREIGN PATENT DOCUMENTS

| | | |
|---|---|---|
| 2 247 838 | 3/1992 | United Kingdom . |
| 2284156 | 11/1994 | United Kingdom . |
| 9420671 U | 11/1994 | United Kingdom . |
| WO 93/06778 | 4/1993 | WIPO . |

OTHER PUBLICATIONS

Extracts from Peak Performance, Guillermo Mendoza, M.D.; Published 1988.

Extract from 3M Health Care, Peak Flow Meter User Instructions, date unknown.

Primary Examiner—Cary O'Connor
Assistant Examiner—Michael Astorino
Attorney, Agent, or Firm—Jones, Tullar & Cooper, P.C.

[57]         ABSTRACT

A peak flow meter has an element (4) displaceable along a hollow body (2) by the exhalation of a subject, and means for indicating the maximum displacement of that element as a measure of peak flow. Pre-set markers (20) are located at selected positions to indicate selected displacement values. The markers are in the form of elements that are snap-fitted onto the meter body at chosen positions and they have a toothed interengagement (12,28) with the body as they snap-fit into place. Accidental or careless movement of the markers is thereby precluded while permitting ready placement when required

15 Claims, 1 Drawing Sheet

PEAK FLOW METERS

BACKGROUND OF THE INVENTION

This invention relates to peak flow meters for monitoring the peak flow expiratory rate of a subject.

In the treatment of such conditions as asthma it has been recognised that regular sampling of peak flow can reveal a trend in the state of the condition and provide a useful warning to the subject to take action that will prevent the condition worsening. Typically, the physician will assess the subject to establish a normal peak flow expiratory rate and at the same time set lower warning limits. For example, if the performance of the subject falls below a first lower limit set, that indicates that a change of medication is needed, and the subject is instructed to seek immediate medical attention if it falls below a still lower limit.

The normal and warning limit values set will be specific to each subject and can be indicated on the body of the peak flow meter in a number of ways. Thus, it is known to provide markers in the form of self-adhesive stickers of different colours which are placed on the body of the instrument adjacent the reading scale at the appropriate scale values. It is also known to employ an adhesive strip (GB 2247838) which the physician can adjust to show different colour zones over particular peak flow ranges. In another alternative (U.S. Pat. No. 5,246,010), markers in the form of small friction pads are held captive in a channel on the body of the meter and are slid to the appropriate positions along the length of the reading scale, the frictional engagement of the pads deliberately requiring considerable force to displace the pads in order that they will not slide accidentally out of position.

These known forms of marker each have their disadvantages, however. Adhesive elements or strips can peel away in time, especially as the body of the instrument will continually be handled by the subject. The use of friction pads will not prevent the set values being disturbed by rough handling or by tampering, which is likely to occur if only out of curiosity, especially if the subject is a child. If the frictional force is increased to the extent that a child cannot shift the pads, it may become difficult for the physician to set them precisely to the values required.

SUMMARY OF THE INVENTION

According to one aspect of the present invention, there is provided a peak flow meter having an indicator slidably mounted on the body of the meter to be displaceable along a scale on the body by exhalation into the meter to indicate a peak flow value of said exhalation, at least one marker element for indicating a preselected scale value, location means on the body for the attachment of said marker element adjacent the scale of any of a range of positions relative to the extent of the scale, said location means comprising positive engagement means for fixing said marker element at the position of attachment thereof on the body corresponding to the preselected scale value.

According to a further aspect of the invention, a peak flow meter is provided having an indicator slidably mounted on a body of the meter to be displaced along a scale on the body by exhalation into the meter to indicate a peak flow value of said exhalation, the body being provided with location means comprising an elongate element extending parallel to the scale, at least one marker element attachable to the location means at any of a range of positions along the length of the elongate element, thereby to indicate a preselected peak flow value for comparison with the value shown by the indicator, and positive engagement means for fixing the marker element at the position of attachment thereof corresponding to the preselected scale value.

Preferably there are respective engagement means for securing the element to the location means and for fixing the position of the element relative to the scale. In a single arrangement, the or each marker element is secured to the location means by a snap-fitting engagement therewith.

Conveniently, the location means comprises a channel extending along at least a portion of the length of the scale and into which said at least one marker element projects. At least one face of the channel may comprise a rib formation over which said at least one element is engaged, and the positive engagement means can be located to the side of the rib formation remote from the channel, or the rib itself.

In a preferred form of the invention, the positive engagement means comprises a toothed rack and said at least one marker element has toothing that can be meshed with the rack.

By way of example, an embodiment of the invention will be described in more detail with reference to the accompanying drawings.

DESCRIPTION OF THE PREFERRED EMBODIMENT

Figure 1:
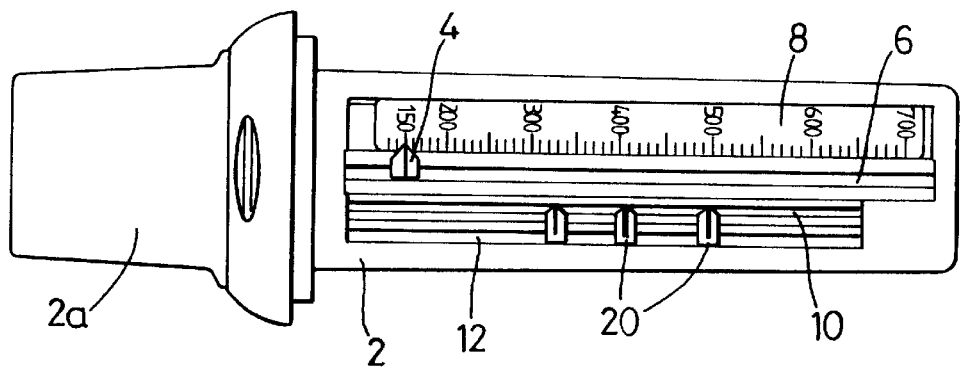
FIG. 1 is a side view of the body of a peak flow meter according to the invention.
Figure 2:
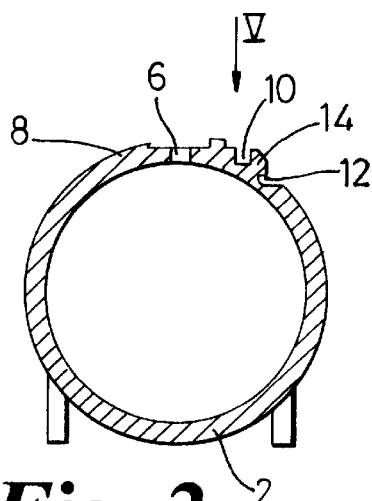
FIG. 2 is a transverse cross-section of the instrument body shown in FIG. 1.
Figure 4:
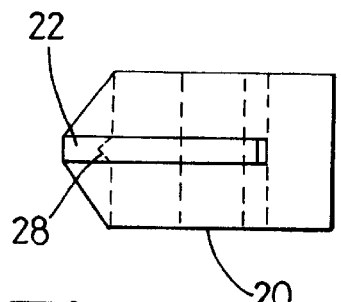
FIG. 4 is a plan view of the marker element in FIG. 3.
Figure 5:
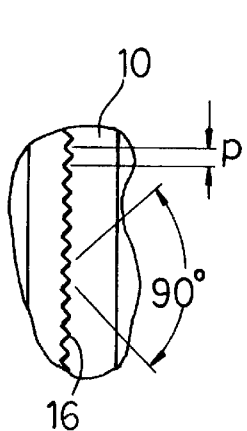
FIG. 5 is a detail drawing in the direction V in FIG. 2, showing the toothed rack in the body channel.

The peak flow meter of the illustrated embodiment may be generally of the form described in U.S. Pat. No. 3,958,565, the content of which is incorporated herein by reference, comprising a hollow cylindrical body 2 into which the subject exhales through a mouthpiece 2a. A piston (not shown) held within the body in a forward position near the mouthpiece by a return spring (not shown) is driven by the exhaled air, against the force of the spring, rearwards along the body. The accompanying drawings show only the cylindrical body 2 of the meter in which the unillustrated spring-loaded piston mechanism may take the same form as in the prior art instrument already referred to, so this mechanism need not be further described here.

As the piston is displaced by the exhaled air, it entrains a scale indicator in the form of pointer 4 that is frictionally engaged with a through-slot 6 extending along the body 2. The slot 6 is progressively opened to the body interior in front of the piston as the piston is displaced, so allowing the air exhaled into the body to escape more freely the greater the displacement. The pointer 4 is entrained along its slot 6 by the displacement of the piston and the maximum displacement of the piston is dependent on the peak rate of flow. When the exhalation ends the piston is returned by the spring to its forward position but friction retains the pointer 4 in its displaced position to indicate a peak flow value against a scale 8 marked along the slot.

Figure 3:
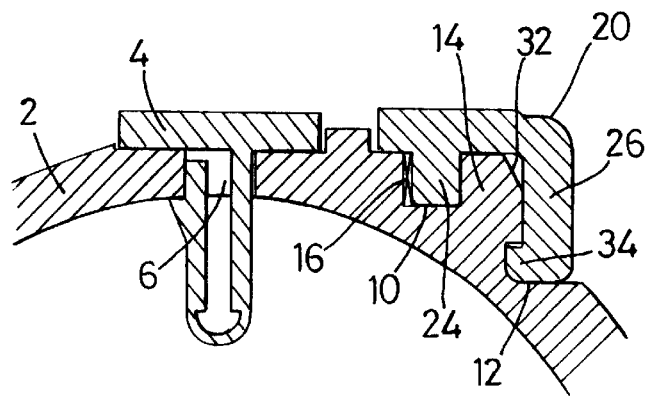
FIG. 3 is a partial view of the transverse cross-section to a larger scale showing a portion of the body with the scale pointer of the instrument and a marker element in place.

To the side of the slot 6 opposite the scale 8, a pair of channels 10, 12 extend parallel to the slot over a greater part of the length of the slot, defining between them a rib formation 14. The channel 10 has a side face formed as a toothed rack 16 consisting of a continuous series of 90° V-profile teeth, their apices extending perpendicular to the channel. The teeth have a relatively fine pitch p, eg. 0.5 mm, and the channel 10 may be some 75 mm or more in length. The second channel 12 is formed parallel to the first channel 10 but at an angle thereto, and shown in FIG. 3, so that the rib formation 14 is partly undercut by the channel 12.

A marker element 20, formed as a moulding of resilient plastics material, can be snapped-fitted onto the body 2 over the rib formation 14 to locate a pointer 22 on its top face opposite a chosen value on the scale 8. The marker element 20 comprises a pair of legs 24,26 for engagement in the respective channels 10,12 and between which the rib formation 14 is located. The first leg 24 has a 90° V-tooth 28 formed on one face opposite the toothing of the rack 16 and the width of the leg 24 is almost as great as the width of the channel 10, so that when the leg 24 is inserted into the channel it is engaged by the rack 16 and cannot slide along the channel.

To set the marker element 20 in place, it is initially located with the first leg 24 above the channel 10 at the required scalar position along the length of the slot, the other leg 26 resting on chamfer 32 on the rib 14. The element 20 is then pressed downwards to splay the legs 24,26 apart resiliently as the tooth 28 slides into place between a pair of corresponding teeth of the rack 16 and in-turned tip or hook 34 of the second leg 26 slides down the lead-in chamfer 32. As the first leg 24 comes towards the bottom of its channel 10, the hook 34 of the second leg 26 is able to snap into the second channel 12. The marker element is thus firmly fixed in position on the body with its pointer 22 indicating a chosen value on the scale. In practice two or more marker elements of different colours will be fixed at different locations to indicate chosen normal and warning values.

The snap-fitting engagement of the marker elements 20 takes place with a relatively large deformation of the legs 24,26 of each element so that they cannot be easily sprung apart and removed. This effect is assisted by the fact that attachment of the elements is facilitated by the lead-in chamfer 32. Preferably, the dimensions are so chosen that an attempt to remove a marker element results in permanent deformation or fracture of the element. In this way it can be ensured that a particular value can be set by clinical staff and will not be disturbed, whether deliberately or accidentally, without their knowledge.

Many modifications of the illustrated embodiment may be made within the scope for the invention. For example, the toothed rack may be formed on the rib formation or in either of the channels 10,12. It is also possible to provide position engagement means on other forms. In another modification, the continuous elongate channels and rib formation are dispensed with and instead locations are provided for the marker elements by a series of discrete engagement means spaced along at least a portion of the length of the scale. It is also possible to provide engagement means that require the use of an instrument or tool to shift or remove an attached marker element.

I claim:

1. A peak flow meter, comprising:

a body;

a peak flow value scale on the body;

an indicator displaceable along the body by exhalation into the body to indicate a peak flow value for said exhalation;

at least one marker element for indicating a preselected value on said scale;

location means on the body for the attachment of said marker element adjacent the scale at any of a range of positions relative to the extent of the scale;

said location means comprising positive engagement means for fixing said at least one marker element at the position of attachment thereof on the body corresponding to the preselected scale value.

2. A meter according to claim 1 having respective interlocking attachment means for securing the at least one marker element to the location means and for fixing the position of the at least one marker element relative to the scale.

3. A meter according to claim 1 comprising snap-fitting engagement elements for securing the or each marker element to the location means.

4. A meter according to claim 1, wherein the location means comprises a channel extending along at least a portion of the length of the scale and into which said at least one marker element projects.

5. A meter according to claim 4, wherein said interlocking attachment means comprises uniformly spaced engagement elements arranged in a series extending parallel to the channel.

6. A meter according to claim 5, wherein the interlocking attachment means comprises a toothed rack on the meter body and toothing on the or each said marker element for meshing engagement with said rack.

7. A meter according to claim 1, wherein said interlocking attachment means comprises complementary engaging elements on the meter body and said at least one marker element, said complementary engaging elements being slidably interengageable to locate the or each marker element in its selected position before it has been secured in place in said position.

8. A meter according to claim 7, wherein the interlocking attachment means comprises a toothed rack on the meter body and toothing on the or each said marker element for meshing engagement with said rack.

9. A peak flow meter, comprising:

a body;

a peak flow value scale on the body;

an indicator displaceable along the body by exhalation into the body to indicate a peak flow value for said exhalation;

at least one marker element for indicating a preselected value on said scale;

location means on the body comprising an elongate element extending parallel to the scale for the attachment of said marker element adjacent the scale at any of a range of positions relative to the extent of the scale;

interlocking attachment means fixing said at least one marker element at the position of attachment thereof on said location means corresponding to the preselected scale value.

10. A peak flow meter comprising:

a body;

a peak flow value scale on said body;

an indicator displaceable along said body by exhalation into said body to indicate a peak flow value for said exhalation;

at least one marker element for indicating a preselected value on said scale;

an elongate element extending parallel to said scale for the attachment of said at least one marker element adjacent to said scale at any range of positions relative to the extent of said scale; and an interlocking attachment means for removably attaching said at least one marker element at a desired position on said elongate element in a manner whereby said at least one marker element is positively engaged with said elongate element such that said positive engagement prevents sliding of said at least one marker element relative to said scale.

11. A meter according to claim 10 wherein said elongate element includes an elongate toothed rack on the body of said meter, and further wherein said at least one marker element includes toothing for meshing with said toothed rack for forming said positive engagement.

12. A meter according to claim 10 wherein said at least one marker element is configured relative to said interlocking attachment means to enable a snap-fitting engagement between said at least one marker element and said interlocking attachment means.

13. A meter according to claim 10 wherein said at least one marker element and said interlocking attachment means are configured to enable said at least one marker element to be removed, repositioned, and reattached on said elongate element without the use of tools.

14. A meter according to claim 10 wherein said elongate element includes a first positive engagement feature and wherein said at least one marker element includes a second positive engagement feature for intermeshing with said first positive engagement feature for forming said positive engagement when said at least one marker element is attached to said elongate element.

15. A meter according to claim 14 wherein said first positive engagement feature is a toothed rack and said second positive engagement feature is toothing on said at least one marker element.

* * * * *